(12) United States Patent
Senko

(10) Patent No.: US 11,650,208 B2
(45) Date of Patent: May 16, 2023

(54) DECONVOLVING ISOBARIC REPORTER ION RATIOS

(71) Applicant: Thermo Finnigan LLC, San Jose, CA (US)

(72) Inventor: Michael W. Senko, Sunnyvale, CA (US)

(*) Notice: Subject to any disclaimer, the term of this patent is extended or adjusted under 35 U.S.C. 154(b) by 334 days.

(21) Appl. No.: 17/151,492

(22) Filed: Jan. 18, 2021

(65) Prior Publication Data

US 2021/0164990 A1    Jun. 3, 2021

Related U.S. Application Data

(62) Division of application No. 15/844,233, filed on Dec. 15, 2017, now Pat. No. 10,895,578.

(51) Int. Cl.
*G01N 33/68* (2006.01)
*G01N 30/72* (2006.01)
*H01J 49/04* (2006.01)
*H01J 49/00* (2006.01)

(52) U.S. Cl.
CPC ......... *G01N 33/6848* (2013.01); *G01N 30/72* (2013.01); *H01J 49/0036* (2013.01); *H01J 49/04* (2013.01); *G01N 2560/00* (2013.01)

(58) Field of Classification Search
None
See application file for complete search history.

(56) References Cited

U.S. PATENT DOCUMENTS

| | | |
|---|---|---|
| 8,236,565 B2 | 8/2012 | Purkayastha et al. |
| 2012/0261568 A1 | 10/2012 | Coon et al. |
| 2015/0293058 A1 | 10/2015 | Wuhr et al. |
| 2016/0139140 A1 | 5/2016 | Thompson et al. |
| 2017/0350861 A1 | 12/2017 | Harder et al. |
| 2018/0209985 A1 | 7/2018 | Braun et al. |

FOREIGN PATENT DOCUMENTS

| | | |
|---|---|---|
| CN | 101454488 A | 6/2009 |
| CN | 107462623 A | 12/2017 |

OTHER PUBLICATIONS

Bamberger et al., "Interference-Free Proteome Quantification with MS/MS-based Isobaric Isotopologue Detection", Journal of Proteome Research, vol. 13 (3), 2014, pp. 1494-1501.
Cappadona et al., "Current challenges in software solutions for mass spectrometry-based quantitative proteomics", Amino Acids (2012), 43 (3), pp. 1087-1108.

(Continued)

*Primary Examiner* — Xiaoyun R Xu

(57) ABSTRACT

A method includes applying distinct isobaric tags to each of a plurality of samples; combining the samples; performing a separation of species within the combined samples; isolating and fragmenting labeled parent ions within a m/z range to produce a plurality of reporter ions, each reporter ion corresponding to one of the isobaric tags; determining intensities of the plurality of reporter ions and ions representative of a parent species at a plurality of points along a peak; and fitting the intensity of the ions representative of a parent species and the plurality of reporter ions at the plurality of points to obtain a relative abundance of the parent species in each of the plurality of samples.

12 Claims, 6 Drawing Sheets

(56) References Cited

OTHER PUBLICATIONS

Erickson et al., "Evaluating Multiplexed Quantitative Phosphopeptide Analysis on a Hybrid Quadrupole Mass Filter/Linear Ion Trap/Orbitrap Mass Spectrometer", Analytical Chemistry 87(2), 2015 pp. 1241-1249.
Huang et al., "Quantitative Proteomic Analysis of Histone Modifications", Chem. Rev. 2015, 115, pp. 2376-2418.
Karpievitch et al., "Liquid chromatography mass spectrometry-based proteomics: Biological and technological aspects", The Annals of Applied Statistics, 2010, vol. 4 (4), pp. 1797-1823.
McAlister et al., "MultiNotch MS3 Enables Accurate, Sensitive, and Multiplexed Detection of Differential Expression across Cancer Cell Line Proteomes", Anal. Chem., 2014, 86, pp. 7150-7158.
Meija et al., "Deconvolution of isobaric interferences in mass spectra", American Society for Mass Spectrometry, vol. 15 (5), 2004, pp. 654-658.
Rauniyar et al., "Isobaric Labeling-Based Relative Quantification in Shotgun Proteomics," J. Proteome Res., 2014 (13), 5293-5309.
Savitski, et al., "Measuring and Managing Ratio Compression for Accurate iTRAQ/TMT Quantification", J. Proteome Res. 2013, 12, 3586-3598.
Schulze et al., "Quantitation in Mass-Spectrometry-Based Proteomics", Annual Review of Plant Biology, vol. 61 (1), pp. 491-516.
Ting et al., "MS3 eliminates ratio distortion in isobaric multiplexed quantitative proteomics," Nature Methods, XP055521887, vol. 8, No. 11 (2011), pp. 937-942.

DECONVOLVING ISOBARIC REPORTER ION RATIOS

CROSS-REFERENCE TO RELATED APPLICATION

This application is a divisional under 35 U.S.C. § 121 and claims the priority benefit of co-pending U.S. patent application Ser. No. 15/844,233, filed Dec. 15, 2017, the disclosure of which is incorporated herein by reference.

FIELD

The present disclosure generally relates to the field of mass spectrometry including deconvolving isobaric reporter ion ratios.

INTRODUCTION

Mass spectrometry has been increasingly used to perform quantification of proteins and peptides, due in part to its ability to concurrently analyze numerous proteins in a sample with high resolution and low detection limits. In many proteomics studies, there is a need to analyze a large number of samples, each containing many individual proteins or peptides. Such large-scale studies have motivated researchers to develop strategies to increase the number of samples that can be analyzed in a given time period. One strategy for increasing sample throughput is multiplexing, where several samples are combined and tested together in a mass spectrometer. With multiplexing, a unique chemical label can be used with each sample of peptides so that a particular peak in a mass spectrum can be correlated to a particular sample.

An isobaric tag is a type of chemical label that can be used in a multiplexed analysis of peptides. Some examples of commercially available isobaric tags are TMT (Tandem Mass Tag Reagents, Thermo Scientific, Pierce Protein Research Product) and iTRAQ (Isobaric Tagging Relative Absolute Quantitation, SCIEX). A set of isobaric tags can have two or more types, where each type has a reporter portion with a unique mass within the set. Although the reporter portions have a different mass, the isobaric tags include mass-normalizing portions, such that the total mass for each type of tag in the set is the same. The isobaric tag can covalently attach to the analyte to form a tag labeled analyte. Next, the tag labeled analytes can be fragmented using tandem mass spectrometry (e.g., MS2) to cause a reporter ion to be liberated. The abundances of the reporter ions are determined from the acquired product ion spectra. The relative abundance of each type of reporter ion corresponds to the abundance of a particular peptide in the sample.

For example, in a multiplexing study with four different samples, they can each be labeled with an isobaric tag having a unique reporter portion. All of the tag labeled analytes can be co-isolated in a mass spectrometer because they have the same m/z value and in the process be separated from other ions having different m/z values. Next, the isolated ions can be fragmented causing the reporter ions to be cleaved from the analyte. The cleaved reporter ions can then be analyzed with the mass spectrometer. Here, four mass spectral peaks should be measured that correlate to the four types of reporter portions. The abundance value for the reporter portions can then be correlated to a relative peptide concentration for each sample.

The use if data independent acquisition (DIA) is slowly growing because of the simplicity of the method and the belief that it provides a very complete picture of a sample or system, and the improved quality of the data due to instrumentation advancements. However, one great shortcoming of DIA is the perceived incompatibility with sample multiplexing. Under certain circumstances, the accuracy of peptide quantitation determined by the isobaric tagging technique may be compromised due to the presence of interfering species. Using isobaric tags (TMT or iTRAQ) from components that fall within a DIA isolation window and also overlap chromatographically will produce distorted ratios. In such a case, the ion isolation step can include two or more tag labeled analyte species that fall within the mass isolation window and chromatographic isolation window. As a result, two or more tag labeled analytes can contribute to the reporter group signal and thereby render inaccurate the measurement of the abundance of the associated peptides. It should be noted that the reporter portion becomes anonymous (i.e., the identity of the precursor ion from which it was formed is lost) once it is cleaved from the peptide. Thus, the cleaved reporter ion intensity signal cannot be later processed to remove the effects of interfering co-isolated ions. This means each sample must be injected serially, resulting in very long acquisition times for large studies. As such, there remains a need for improved tagging techniques that increases the accuracy in quantitation of peptides with mass spectrometry, especially in the context of DIA.

SUMMARY

In a first aspect, a method can include applying distinct isobaric tags to each of a plurality of samples; combining the samples; performing a separation of species within the combined samples; isolating and fragmenting labeled parent ions within a m/z range to produce a plurality of reporter ions, each reporter ion corresponding to one of the isobaric tags; determining intensities of the plurality of reporter ions and ions representative of a parent species at a plurality of points along a peak; and fitting the intensity of the ions representative of a parent species and the plurality of reporter ions at the plurality of points to obtain a relative abundance of the parent species in each of the plurality of samples.

In various embodiments of the first aspect, performing the separation can include performing a chromatographic separation and the peak can be a chromatographic peak.

In various embodiments of the first aspect, performing the separation can include performing an electrophoretic separation and the peak can be an electrophoretic peak.

In various embodiments of the first aspect, the ions representative of the parent species can include structurally informative ions resulting from fragmenting the labeled parent ions. In particular embodiments, determining the intensity of the ions representative of the parent species can include summing the intensity of a plurality structurally informative ions resulting from fragmenting the labeled parent ions.

In various embodiments of the first aspect, the ions representative of the parent species can include the labeled parent ions; and determining the intensity of the ions representative of a parent species can be based on the intensity of the labeled parent ions. In particular embodiments, the intensity of the labeled parent ions can be measured without fragmenting the ions.

In various embodiments of the first aspect, fitting can include performing a least squares fit.

In various embodiments of the first aspect, the method can further include determining intensities of ions representative of a second parent species at the plurality of points, the plurality of points further including points along a second peak; and wherein fitting to obtain a relative abundance can include fitting the intensity of the ions representative of the parent species, ions representative of the second parent species, and the plurality of reporter ions at the plurality of points. In particular embodiments, the first and second chromatographic peaks can at least partially overlap.

In a second aspect, an analysis system can include a separation instrument, a mass spectrometer, and processor. The separation instrument can be configured to perform a separation of compounds within a combined sample. The combined sample can include a plurality of samples each labeled with a different isobaric tag. The mass spectrometer can include a mass selective device configured to isolate ions within a m/z range; a fragmentation cell configured to fragment the ions within the m/z range; and a ion detector configured to measure the intensities of ions representative of a parent species and a plurality of reporter ions. The processor can be configured fit the intensities of the ions representative of a parent species and the plurality of reporter ions at a plurality of points along a peak to obtain a relative abundance of the parent species in each of the plurality of samples.

In various embodiments of the second aspect, the separation instrument can include a chromatographic separation device.

In various embodiments of the second aspect, the separation instrument can include an electrophoretic separation device.

In various embodiments of the second aspect, the ions representative of the parent species can include structurally informative ions resulting from fragmenting the labeled parent ions.

In various embodiments of the second aspect, the ions representative of the parent species can include the labeled parent ions. In particular embodiments, the intensity of the ions representative of a parent species can be the intensity of the labeled parent ions without fragmentation.

In various embodiments of the second aspect, fitting can include performing a least squares fit.

In various embodiments of the second aspect, the ion detector can be further configured to determine intensities of ions representative of a second parent species at the plurality of points, the plurality of points further including points along a second peak; and wherein the system controller can be configured to fit to obtain a relative abundance by fitting the intensity of the ions representative of the parent species, ions representative of the second parent species, and the plurality of reporter ions at the first and second plurality of points. In particular embodiments, the first and second peaks at least partially overlap.

In a third aspect, a non-transitory computer readable medium can contain instructions that when implemented by a processor can perform the steps of: obtaining intensities data generated by a mass spectrometer for ions representative of a parent species and a plurality of reporter ions at a plurality of points along a peak, the intensity data collected from a combined sample that has undergone a separation of compounds within the sample, the combined sample including a plurality of samples each labeled with a different isobaric tag; and fitting the intensity data of the ions representative of a parent species and the plurality of reporter ions at a plurality of points along a peak to obtain a relative abundance of the parent species in each of the plurality of samples.

In various embodiments of the third aspect, the separation can be a chromatographic separation and the peak can be a chromatographic peak.

In various embodiments of the third aspect, the separation can be an electrophoretic separation and the peak can be an electrophoretic peak.

In various embodiments of the third aspect, the ions representative of the parent species can include structurally informative ions resulting from fragmenting the labeled parent ions.

In various embodiments of the third aspect, the ions representative of the parent species include the labeled parent ions. In particular embodiments, the intensity of the labeled parent ions can be measured without fragmenting the ions.

In various embodiments of the third aspect, fitting can include performing a least squares fit.

In various embodiments of the third aspect, further instructions that when implemented by a processor can perform the steps of using the mass spectrometer to obtain intensity data for ions representative of a second parent species a the plurality of points, the plurality of points further including points along a second peak; and fitting the intensity data of the ions representative of the parent species, the ions representative of the second parent species, and the plurality of reporter ions at the plurality of points to obtain a relative abundance of the parent species and the second parent species in each of the plurality of samples. In particular embodiments, the first and second peaks can at least partially overlap.

DRAWINGS

For a more complete understanding of the principles disclosed herein, and the advantages thereof, reference is now made to the following descriptions taken in conjunction with the accompanying drawings and exhibits, in which.

Figure 1:
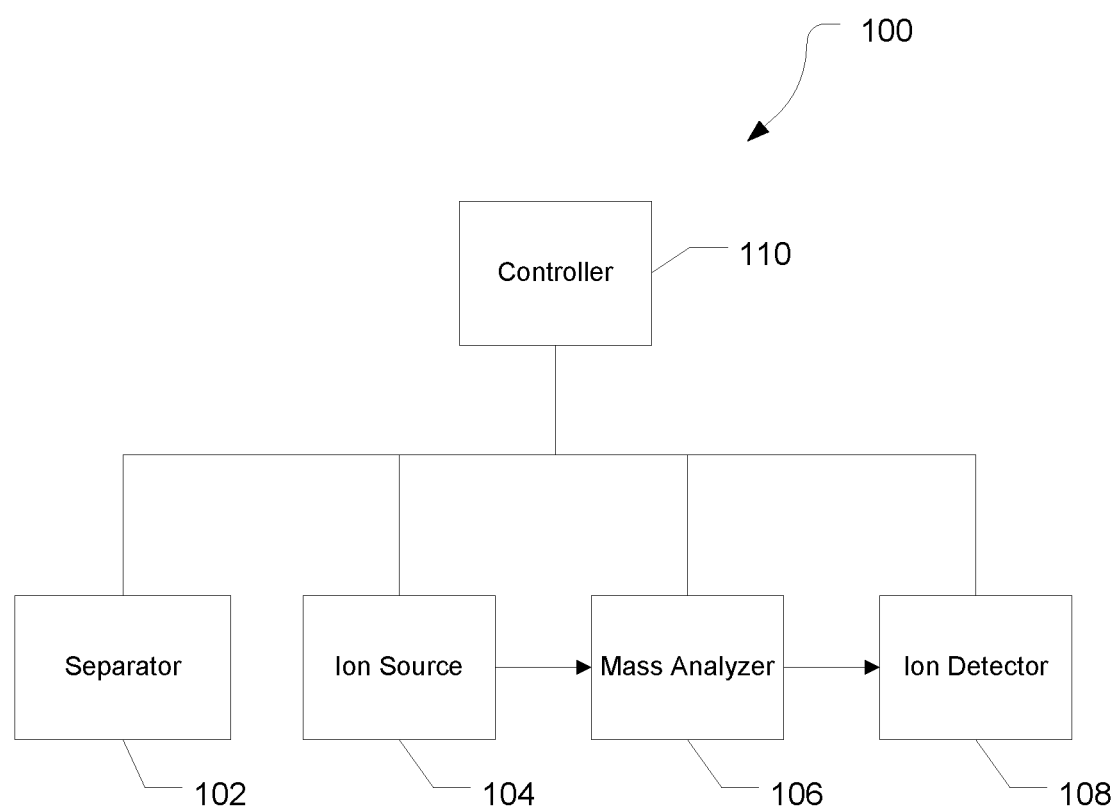
FIG. 1 is a block diagram of an exemplary mass spectrometry system, in accordance with various embodiments.

It is to be understood that the figures are not necessarily drawn to scale, nor are the objects in the figures necessarily drawn to scale in relationship to one another. The figures are depictions that are intended to bring clarity and understanding to various embodiments of apparatuses, systems, and methods disclosed herein. Wherever possible, the same reference numbers will be used throughout the drawings to refer to the same or like parts. Moreover, it should be appreciated that the drawings are not intended to limit the scope of the present teachings in any way.

DESCRIPTION OF VARIOUS EMBODIMENTS

Embodiments of systems and methods for ion isolation are described herein and in the accompanying exhibits.

The section headings used herein are for organizational purposes only and are not to be construed as limiting the described subject matter in any way.

In this detailed description of the various embodiments, for purposes of explanation, numerous specific details are set forth to provide a thorough understanding of the embodiments disclosed. One skilled in the art will appreciate, however, that these various embodiments may be practiced with or without these specific details. In other instances, structures and devices are shown in block diagram form. Furthermore, one skilled in the art can readily appreciate that the specific sequences in which methods are presented and performed are illustrative and it is contemplated that the sequences can be varied and still remain within the spirit and scope of the various embodiments disclosed herein.

All literature and similar materials cited in this application, including but not limited to, patents, patent applications, articles, books, treatises, and internet web pages are expressly incorporated by reference in their entirety for any purpose. Unless described otherwise, all technical and scientific terms used herein have a meaning as is commonly understood by one of ordinary skill in the art to which the various embodiments described herein belongs.

It will be appreciated that there is an implied "about" prior to the temperatures, concentrations, times, pressures, flow rates, cross-sectional areas, etc. discussed in the present teachings, such that slight and insubstantial deviations are within the scope of the present teachings. In this application, the use of the singular includes the plural unless specifically stated otherwise. Also, the use of "comprise", "comprises", "comprising", "contain", "contains", "containing", "include", "includes", and "including" are not intended to be limiting. It is to be understood that both the foregoing general description and the following detailed description are exemplary and explanatory only and are not restrictive of the present teachings.

As used herein, "a" or "an" also may refer to "at least one" or "one or more." Also, the use of "or" is inclusive, such that the phrase "A or B" is true when "A" is true, "B" is true, or both "A" and "B" are true. Further, unless otherwise required by context, singular terms shall include pluralities and plural terms shall include the singular.

A "system" sets forth a set of components, real or abstract, comprising a whole where each component interacts with or is related to at least one other component within the whole.

Mass Spectrometry Platforms

Various embodiments of mass spectrometry platform 100 can include components as displayed in the block diagram of FIG. 1. According to various embodiments, mass spectrometer 100 can include a separator 102, an ion source 104, a mass analyzer 106, an ion detector 108, and a controller 110.

In various embodiments, the separator 102 at least partially separates a sample into individual components. Separator 102 can include a liquid chromatography system, a gas chromatography system, a capillary electrophoresis system, or the like. In various embodiments, the separation of two compounds of the sample can be baseline resolved, such that peaks or bands may not overlap. In other embodiments, the separation of two compounds may be incomplete, such that the peaks or bands of the two compounds partially overlap, such that both compounds are present in fractions within the overlapping region.

In various embodiments, the ion source 104 generates a plurality of ions from a sample. The ion source 104 can include, but is not limited to, a matrix assisted laser desorption/ionization (MALDI) source, electro spray ionization (ESI) source, atmospheric pressure chemical ionization (APCI) source, atmospheric pressure photoionization source (APPI), inductively coupled plasma (ICP) source, electron ionization source, chemical ionization source, photoionization source, glow discharge ionization source, thermospray ionization source, and the like.

In various embodiments, the mass analyzer 106 can separate ions based on a mass to charge ratio of the ions. For example, the mass analyzer 106 can include a quadrupole mass filter analyzer, a quadrupole ion trap analyzer, a time-of-flight (TOF) analyzer, an electrostatic trap (e.g., ORBITRAP mass analyzer) mass analyzer, Fourier transform ion cyclotron resonance (FT-ICR) mass analyzer, and the like. In various embodiments, including when mass analyzer 106 is an ion trap, the mass analyzer 106 can also be configured or include an additional device to fragment ions using resonance excitation or collision cell collision induced dissociation (CID), electron transfer dissociation (ETD), electron capture dissociation (ECD), photo induced dissociation (PID), surface induced dissociation (SID), and the like, and further separate the fragmented ions based on the mass-to-charge ratio.

In various embodiments, the ion detector 108 can detect ions. For example, the ion detector 108 can include an electron multiplier, a Faraday cup, and the like. Ions leaving the mass analyzer can be detected by the ion detector. In various embodiments, the ion detector can be quantitative, such that an accurate count of the ions can be determined. In other embodiments, the functionality of the mass analyzer 106 and ion detector 106 can be combined, such as when using an ORBITRAP mass analyzer.

In various embodiments, the controller 110 can communicate with the separator 102, the ion source 104, the mass analyzer 106, and the ion detector 108. For example, the controller 110 can configure the separator 102, such as by controlling a temperature, a flow rate, a solvent ratio, a current, or the like. For example, the controller 110 can configure the ion source or enable/disable the ion source. Additionally, the controller 110 can configure the mass analyzer 106 to select a particular mass range to detect. Further, the controller 110 can adjust the sensitivity of the ion detector 108, such as by adjusting the gain. Additionally, the controller 110 can adjust the polarity of the ion detector 108 based on the polarity of the ions being detected. For example, the ion detector 108 can be configured to detect positive ions or be configured to detect negative ions.

Isobaric Tags

Figure 2A:
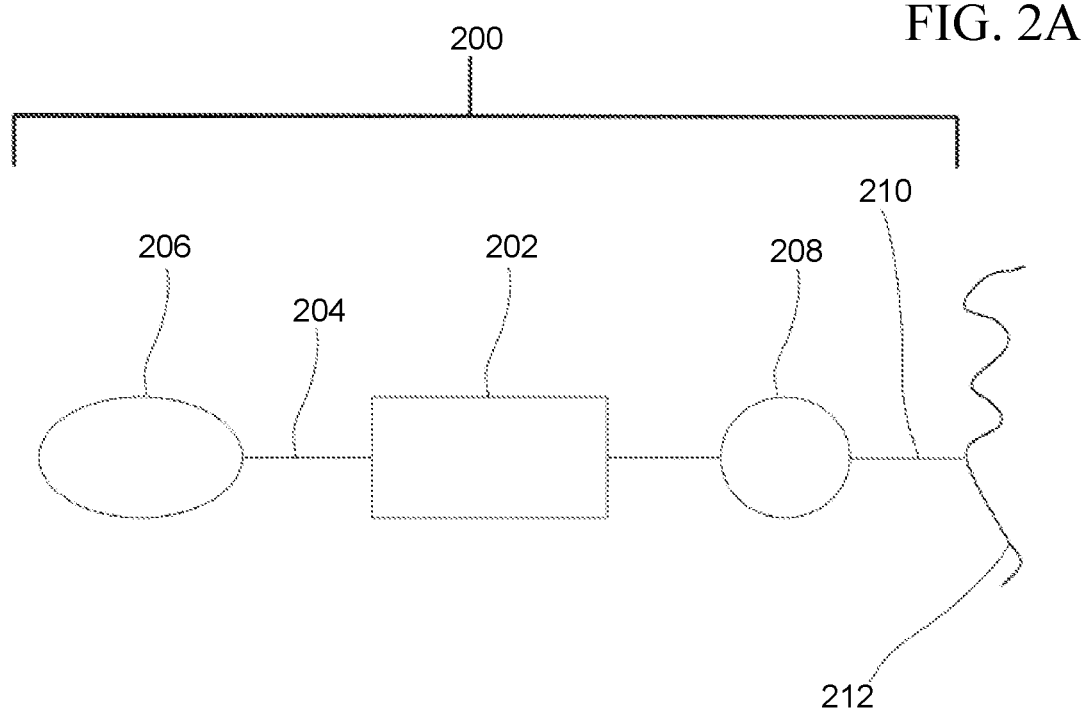
FIG. 2A illustrates a schematic of an isobaric tag that includes a reporter portion, a mass-normalizing portion, and a reactive portion, in accordance with various embodiments.

An isobaric tag will be described where the mass-labeling group is cleaved from the analyte during analysis with a mass spectrometer. Although the analyte has been described as being a protein or peptide, other analyte molecules may be used with the isobaric tags described herein that may include glycans, steroids, nucleotides, sugars, toxins, lipids, and low molecular weight metabolites. FIG. 2A illustrates a schematic of an isobaric tag 200 coupled to an analyte 212. Isobaric tag 200 includes a mass-normalizing group 202 and a mass-labeling group 206. The mass-normalizing group 202 includes a reactive group 208 configured to form a first bond 210 to a functional group of an analyte 212 in a sample. Mass-normalizing group 202 and mass-labeling group 206 are attached via a second bond 204. The attachment of mass-normalizing group 202 to mass-labeling group 206 is not limited to a direct attachment and can include an intermediate or intervening group such as, for example, a spacer group.

Figure 2B:
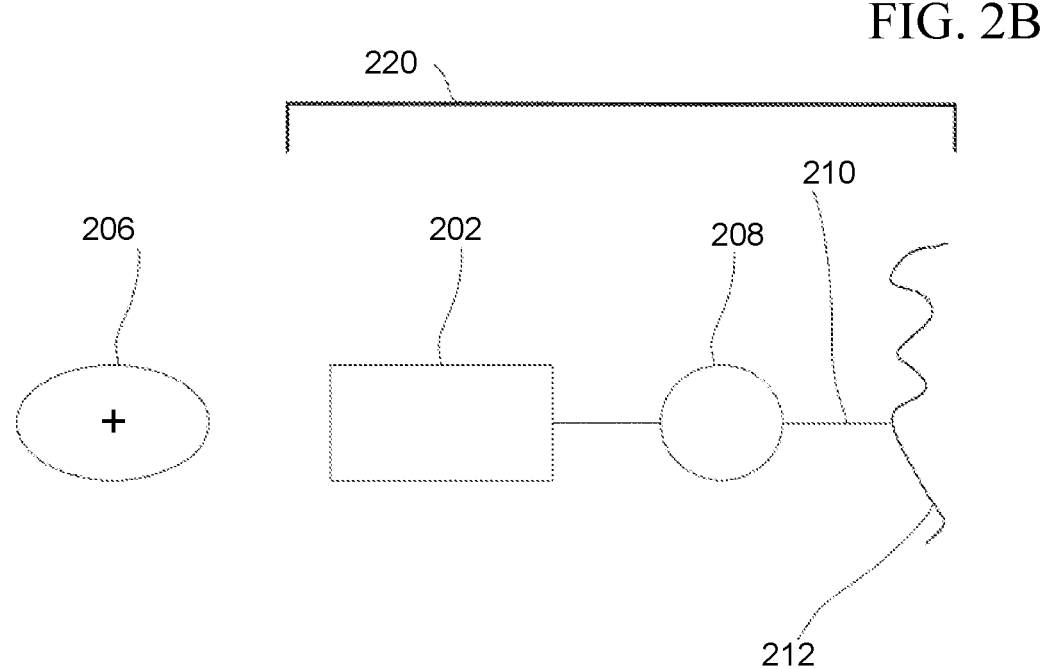
FIG. 2B illustrates a schematic of the isobaric tag of FIG. 2A where the reporter portion has been cleaved off to form a charged reporter ion and leaving a charged mass-labeled analyte, in accordance with various embodiments.

First bond 210 is configured to be stable and not cleave when subjected to a dissociative energy level. When subjected to the same dissociative energy level, second bond 204 is configured to cleave so that mass-labeling group 206 forms a separated charged reporter ion, as illustrated in FIG. 2B. In turn, a remainder portion of the tag forms a mass-labeled neutral molecule or ion 220, as illustrated in FIG. 2B. The relative yield of cleaving second bond 204 of the tag labeled analyte can be about the same for each type of tag in the set. It should be noted that a range of dissociative energy levels to fragment the tag labeled analyte can be selected to optimize the yield of cleaving second bond 204, while at the same time, not cleaving first bond 210, the internal bonds of mass-labeling group 206, and of analyte 212. The dissociative energy levels used in fragmenting the tag labeled analyte may be referred to as standard collisionally activated dissociation (CAD) conditions.

In another embodiment, the analyte portion of the tag labeled analyte can also be partially fragmented so long as there is a measurable amount of the fragmented analyte species. The fragmented analyte species includes a fragmented portion of the analyte that is still attached to the mass-labeling group 206. The analyte portion of the analyte fragment species can fragment in the same way with a similar yield for each type of tag labeled analyte in the set so that relative measurements can be made with respect to each type of tag.

It should be noted, that under certain circumstances, while using the tags described herein, a portion of the tag labeled analytes may cleave at the first bond and/or a portion of the second bond may not cleave when subjected to a dissociative energy level from a mass spectrometer. In this scenario, quantitative or semi-quantitative information can be obtained so long as the yield of the charged mass-labeled analyte is about the same for each type of tag in the set.

Fragmentation techniques such as collisionally activated dissociation (CAD) may be used to fragment the tag labeled analytes. CAD may involve the acceleration of an ion beam (via the application of suitable voltages to electrodes adjacent to the ion path) into a collision region filled with neutral collision gas atoms or molecules (often helium, nitrogen or argon). Alternatively, CAD may be effected within an ion trap by applying a resonant excitation voltage to electrodes of an ion trap, causing the analyte ions to become kinetically excited and consequently undergo energetic collisions with neutral gas atoms or molecules present in the ion trap. As a result of collisions between the analyte ions and the neutral gas, some of the kinetic energy is converted into internal energy, which results in breaking the second bond. In addition, electron-transfer dissociation (ETD) may be used as a fragmentation technique where fragmentation of cations (e.g. peptides or proteins) is induced by transferring electrons to them. ETD is described in more detail in U.S. Pat. No. 7,534,622, which is hereby fully incorporated by reference herein. While the foregoing describes a few dissociation techniques, it should be understood that these descriptions are provided by way of example only, and does not limit the embodiments to any particular technique.

In an embodiment, a set of isobaric tags can include two or more types of tags. Each type of tag has about the same aggregate mass. However, the mass of the mass-labeling group for each type of tag is different. This can be accomplished with a corresponding difference in the mass normalizing group. As such, the mass-normalizing group for each type of tag is also different.

In a first embodiment of a set of isobaric tags, it can include four types of tags. The four types of tags include a first, a second, a third, and a fourth mass-labeling group, respectively. The first mass-labeling group has a primary mass value (n). The second mass-labeling group has a second mass (n+m1) that is greater than the primary mass (n) by a first predetermined mass interval (m1). The third mass-labeling group has a third mass (n+m2) that is greater than the primary mass (n) by a second predetermined mass interval (m2). The fourth mass-labeling group has a fourth mass (n+m3) that is greater than the primary mass (n) by a third predetermined mass interval (m3). Although an embodiment using four types of tags has been described, a set of isobaric tags can range from as few as two types and can also be greater than four types.

The following will describe a method for using isobaric tags in analyzing an analyte such as a peptide. As used herein, the term "peptide" denotes any molecule comprising multiple amino acids linked by peptide bonds, and is intended to include intact proteins as well as protein fragments produced by proteolytic digestion of proteins. Examples of sample types that can be analyzed using the embodiments described herein include any variety of peptide-containing substances, such as cell lysates and biological fluids (e.g., blood, serum, or cerebrospinal fluid (CSF)). Once the samples are collected, they may each be digested with a proteolytic enzyme such as Lys-C or trypsin to produce peptides, some of which may serve as surrogates for the protein from which they are derived.

As an example, two different samples can be analyzed at the same time. The first and second samples have a first and second, concentration of the analytes, respectively. The analyte can be a particular peptide resulting from the protein digest. In a first tube, a first sample can be incubated with a first type of tag to form a first tag labeled analyte. The incubation step is a labeling process that includes a time period where a reactive group of the tag can react with an analyte to form a tag labeled analyte. The first tag labeled analyte includes a first mass-normalizing portion coupled to the analyte via a first bond and a first mass-labeling portion coupled to the first mass-normalizing portion via a second bond.

In a second tube, a second sample can be incubated with a second type of tag to form a second tag labeled analyte. The second tag labeled analyte includes a second mass-normalizing portion coupled to the analyte via a first bond and a second mass-labeling portion coupled to the second mass-normalizing portion via a second bond.

The contents of the first and second tubes can be combined together to form a sample mixture. Next, the sample mixture can be fractionated or cleaned up such as, for example, by using strong cation exchange chromatography column (i.e., SCX). To separate the various peptides in the sample mixture, liquid chromatography techniques can be used such as, for example, high pressure liquid chromatography (HPLC) or capillary chromatography. The chromatography effluent can then be injected into a mass spectrometer. Assuming that the first and second tag labeled analytes have the same chemical structure, then all of the tag labeled analytes should elute at the same time. In most situations, changing the isotopes of carbon and nitrogen atoms of a molecule does not affect the chromatographic elution times.

The effluent can be ionized with an ionization device in the mass spectrometer and a particular m/z range of ions can be isolated, for example by applying a suitable resonant isolation waveform to an ion trap, or by selective transmission through a quadrupole mass filter. The first and second tag labeled analytes can be co-isolated because they have the same mass. Other ions that have a different mass-to-charge ratio than the tag labeled analytes will be excluded from the ion trap. Next, all of the co-isolated tag labeled analytes can be subjected to a dissociative energy level with a mass spectrometer using a technique such as collisionally activated dissociation.

The second bond for all of the tag labeled analytes can be cleaved to form a charged reporter portion and a charged mass-normalized analyte. Thus, after the cleaving step, the first and second tag labeled analytes form a, respectively, first and second, charged mass-labeled analytes. In addition to forming charged mass-labeled analytes after the cleaving step, the first and second reporter portions form a separated charged species.

All of the charged reporter portion, that were formed after cleaving from the mass-normalizing groups, can be measured in a mass analyzer of a mass spectrometer. In alternate embodiments, the charged mass-labeled analytes can be measured in the mass analyzer after cleaving off the reporter portion. The measured mass-to-charge ratios for each of the reporter portions (or charged mass-labeled analytes) are different because each type of mass-labeling group has a unique mass. This allows each of the samples to be quantified based on the corresponding peak magnitude of the mass spectrum. The first and second concentration can be calculated based on the abundance value of the respective mass-to-charge ratios.

Figure 3:
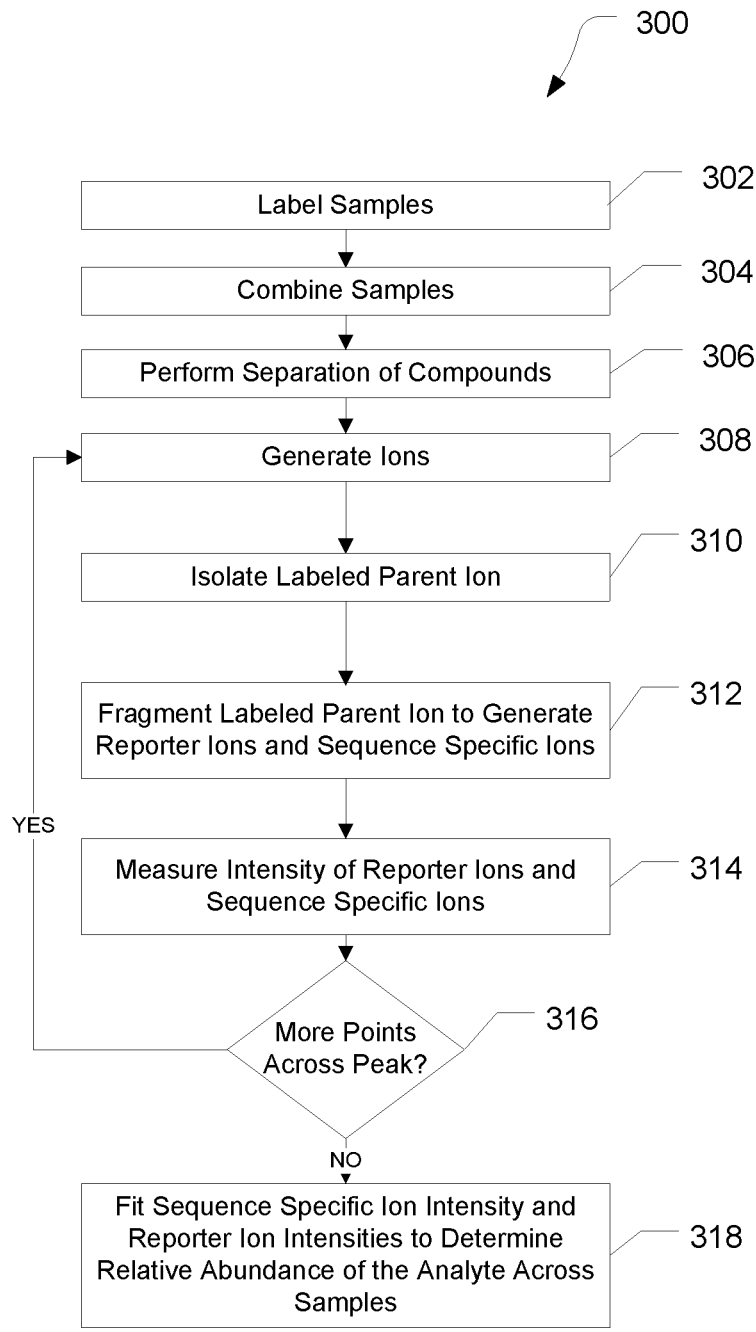
FIG. 3 is a flow diagram illustrating an exemplary method of determining the relative abundance of one or more parent ions across a plurality of samples, in accordance with various embodiments.

FIG. 3 illustrates an exemplary method of determining the relative abundance of one or more analytes across a plurality of samples. At 302, the samples can be labeled using isobaric tags, such as by using the method discussed above. At 304, the samples can be combined, and at 306, a separation can be performed on the combined sample to separate individual compounds. In various embodiments, the separation can be a chromatographic separation, an electrophoretic separation, or other separation technique known in the art that can at least partially separate various analyte compounds within the combined sample.

At 308, ions can be generated from the separated, pooled samples, such that for a given analyte, there can be multiple corresponding labeled analytes such that each unique label corresponds to one of the samples.

At 310, a labeled parent ion can be isolated by selecting a mass range corresponding to the labeled parent ion. The mass of the parent ion can be the sum of the mass of the compound and the mass of the label and linker.

At 312, the labeled parent ions can be fragmented to generate reporter ions and structurally informative ions. In various embodiments, the reporter ions and structurally informative ions can be generated from different fragmentation events, with the reporter ions created by cleaving the tag portion of the parent ion and the structurally informative ions generated by cleaving the peptide backbone of the parent ion. At 314, the intensity of the reporter ions and structurally informative ions can be measured.

At 316, it can be determined if there are additional data points that can be obtained across a separation peak of the analyte. In various embodiments, an analyte can elute from the chromatographic column over a period of time, generally producing a peak having a Gaussian shape. Other separation techniques can also generate peaks or bands of the analyte as the analyte with similar properties. The period of time can be significantly longer than the time needed to perform the mass analysis (steps 308, 310, 312, and 314), such that mass spectrometry data can be obtained at multiple points across the peak. When there is time available for collecting additional mass spectrometry data of the analyte, additional mass analysis can be perform by returning to 308.

At 318, when sufficient points are collected, a fit of the structurally informative ion intensity and the reporter ion intensities can be performed to determine the relative abundance of the analyte the samples. In various embodiments, the amount of a reporter ion (R) can include contributions from the parent ion (P) and other interfering ions (O). Additionally, since only tagged ions from a specific sample produce a specific reporter ion, there is a contribution quotient for the parent ion (p) and the other interfering ions (o). Thus, $R=p*P+o*O$. The contribution of other ions can be considered relatively constant, simplifying to $R=p*P+c$. A fit can be performed using the multiple measurements of R and P to determine the value of p. In various embodiments, each sample (reporter ion) can be fit independently resulting values for $p1, p2, \ldots, pn$. Then, the relative abundance of the compound in each sample can be determined based on the relative values for $p1, p2, \ldots, pn$. In other embodiments, the multiple samples can be fit simultaneously.

In alternate embodiments, the intensity of the parent ion can be obtained prior to fragmentation and the parent ion intensity can be used during the fit instead of the structurally informative ion intensity.

In various embodiments, the fit can be performed using a linear least squares fitting algorithm. In other embodiments, other fitting algorithms known in the art can be used.

In various embodiments, two analytes can be only partially separated by the separation, such that there is an overlapping portion between the two analytes. In such embodiments, it can be advantageous to collect mass spectrometry data across both peaks. The parent ion intensities and reporter ion intensities from the data points across both peaks can be fit to obtain the relative abundance of both analytes across the samples. Modifying the above equation to account for the contribution of two partially resolved parent ions results in $R=pa*Pa+pb*Pb+c$, where pa and Pa correspond to one compound and pb and Pb correspond to the other compound. By collecting data points across the range of both peaks, the number of data points can be increased sufficiently to adequately fit the increased number of parameters.

Computer-Implemented System

Figure 4:
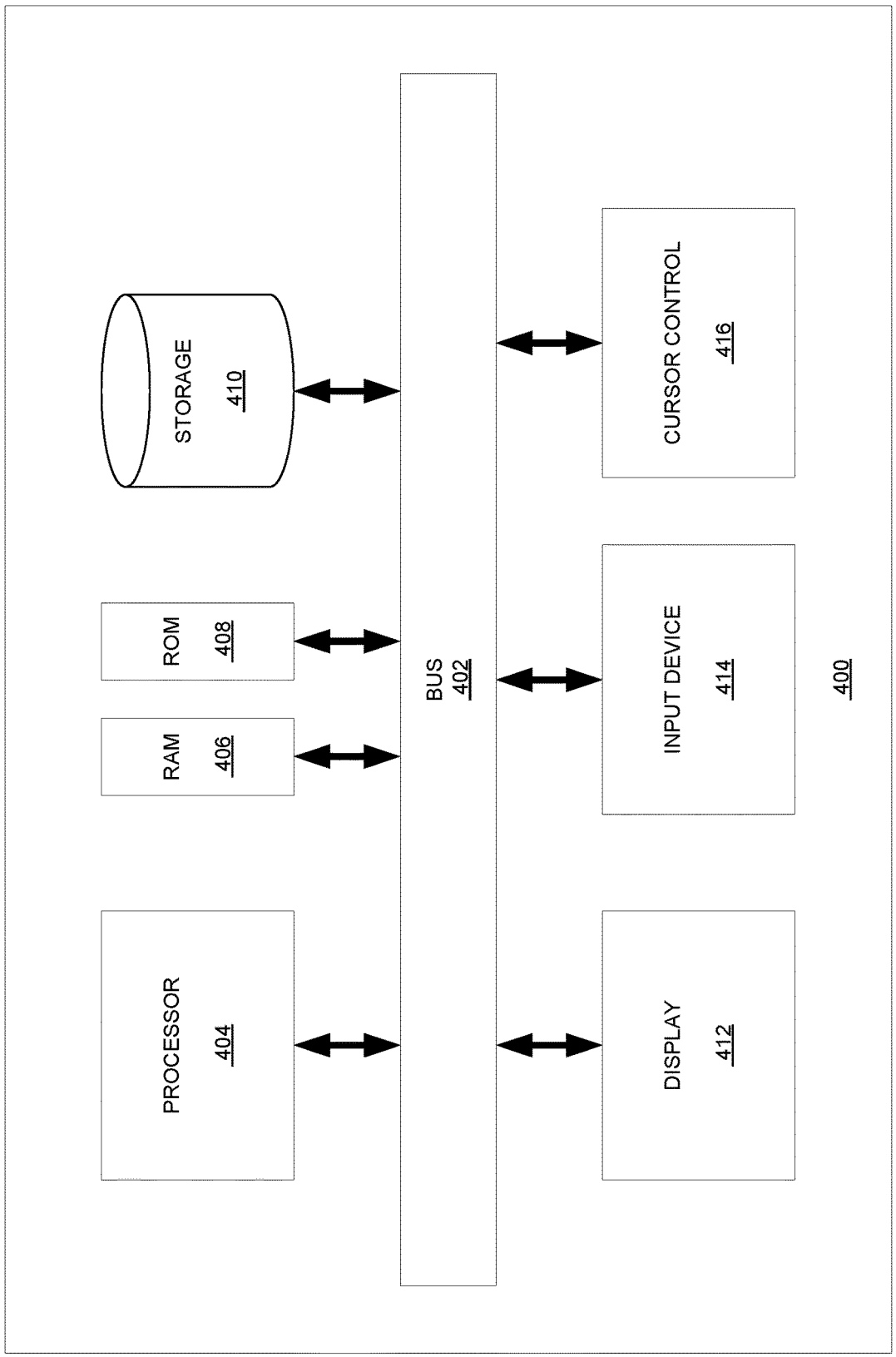
FIG. 4 is a block diagram illustrating an exemplary computer system.

FIG. 4 is a block diagram that illustrates a computer system 400, upon which embodiments of the present teachings may be implemented as which may incorporate or communicate with a system controller, for example controller 108 shown in FIG. 1, such that the operation of components of the associated mass spectrometer may be adjusted in accordance with calculations or determinations made by computer system 400. In various embodiments, computer system 400 can include a bus 402 or other communication mechanism for communicating information, and a processor 404 coupled with bus 402 for processing information. In various embodiments, computer system 400 can also include a memory 406, which can be a random access memory (RAM) or other dynamic storage device, coupled to bus 402, and instructions to be executed by processor 404. Memory 406 also can be used for storing temporary variables or other intermediate information during execution of instructions to be executed by processor 404. In various embodiments, computer system 400 can further include a read only memory (ROM) 408 or other static storage device coupled to bus 402 for storing static information and instructions for processor 404. A storage device 410, such as a magnetic disk or optical disk, can be provided and coupled to bus 402 for storing information and instructions.

In various embodiments, computer system 400 can be coupled via bus 402 to a display 412, such as a cathode ray tube (CRT) or liquid crystal display (LCD), for displaying information to a computer user. An input device 414, including alphanumeric and other keys, can be coupled to bus 402 for communicating information and command selections to processor 404. Another type of user input device is a cursor control 416, such as a mouse, a trackball or cursor direction keys for communicating direction information and command selections to processor 404 and for controlling cursor movement on display 412. This input device typically has two degrees of freedom in two axes, a first axis (i.e., x) and a second axis (i.e., y), that allows the device to specify positions in a plane.

A computer system 400 can perform the present teachings. Consistent with certain implementations of the present teachings, results can be provided by computer system 400 in response to processor 404 executing one or more sequences of one or more instructions contained in memory 406. Such instructions can be read into memory 406 from another computer-readable medium, such as storage device 410. Execution of the sequences of instructions contained in memory 406 can cause processor 404 to perform the processes described herein. In various embodiments, instructions in the memory can sequence the use of various combinations of logic gates available within the processor to perform the processes describe herein. Alternatively hardwired circuitry can be used in place of or in combination with software instructions to implement the present teachings. In various embodiments, the hard-wired circuitry can include the necessary logic gates, operated in the necessary sequence to perform the processes described herein. Thus implementations of the present teachings are not limited to any specific combination of hardware circuitry and software.

The term "computer-readable medium" as used herein refers to any media that participates in providing instructions to processor 404 for execution. Such a medium can take many forms, including but not limited to, non-volatile media, volatile media, and transmission media. Examples of non-volatile media can include, but are not limited to, optical or magnetic disks, such as storage device 410. Examples of volatile media can include, but are not limited to, dynamic memory, such as memory 406. Examples of transmission media can include, but are not limited to, coaxial cables, copper wire, and fiber optics, including the wires that comprise bus 402.

Common forms of non-transitory computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, PROM, and EPROM, a FLASH-EPROM, any other memory chip or cartridge, or any other tangible medium from which a computer can read.

Certain embodiments can also be embodied as computer readable code on a computer readable medium. The computer readable medium is any data storage device that can store data, which can thereafter be read by a computer system. Examples of the computer readable medium include hard drives, network attached storage (NAS), read-only memory, random-access memory, CD-ROMs, CD-Rs, CD-RWs, magnetic tapes, and other optical and non-optical data storage devices. The computer readable medium can also be distributed over a network coupled computer systems so that the computer readable code is stored and executed in a distributed fashion.

In accordance with various embodiments, instructions configured to be executed by a processor to perform a method are stored on a computer-readable medium. The computer-readable medium can be a device that stores digital information. For example, a computer-readable medium includes a compact disc read-only memory (CD-ROM) as is known in the art for storing software. The computer-readable medium is accessed by a processor suitable for executing instructions configured to be executed.

In various embodiments, the methods of the present teachings may be implemented in a software program and applications written in conventional programming languages and on conventional computer or embedded digital systems.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Further, in describing various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art can readily appreciate that the sequences may be varied and still remain within the spirit and scope of the various embodiments.

The embodiments described herein, can be practiced with other computer system configurations including hand-held devices, microprocessor systems, microprocessor-based or programmable consumer electronics, minicomputers, mainframe computers and the like. In various embodiments, instrument control and data analysis can be performed by the same computer system. In other embodiments, instrument control and data analysis can be performed separately by two or more computer systems. In still other embodiments, the computer system performing instrument control and can perform a portion of the data analysis and one or more other computer systems can perform additional data analysis. The embodiments can also be practiced in distributing computing environments where tasks are performed by remote processing devices that are linked through a network.

It should also be understood that the embodiments described herein can employ various computer-implemented operations involving data stored in computer systems. These operations are those requiring physical manipulation of physical quantities. Usually, though not necessarily, these quantities take the form of electrical or magnetic signals capable of being stored, transferred, combined, compared, and otherwise manipulated. Further, the manipulations performed are often referred to in terms, such as producing, identifying, determining, or comparing.

Any of the operations that form part of the embodiments described herein are useful machine operations. The embodiments, described herein, also relate to a device or an apparatus for performing these operations. The systems and methods described herein can be specially constructed for the required purposes or it may be a general purpose computer selectively activated or configured by a computer program stored in the computer. In particular, various general purpose machines may be used with computer programs written in accordance with the teachings herein, or it may be more convenient to construct a more specialized apparatus to perform the required operations.

Results

Figure 5A:
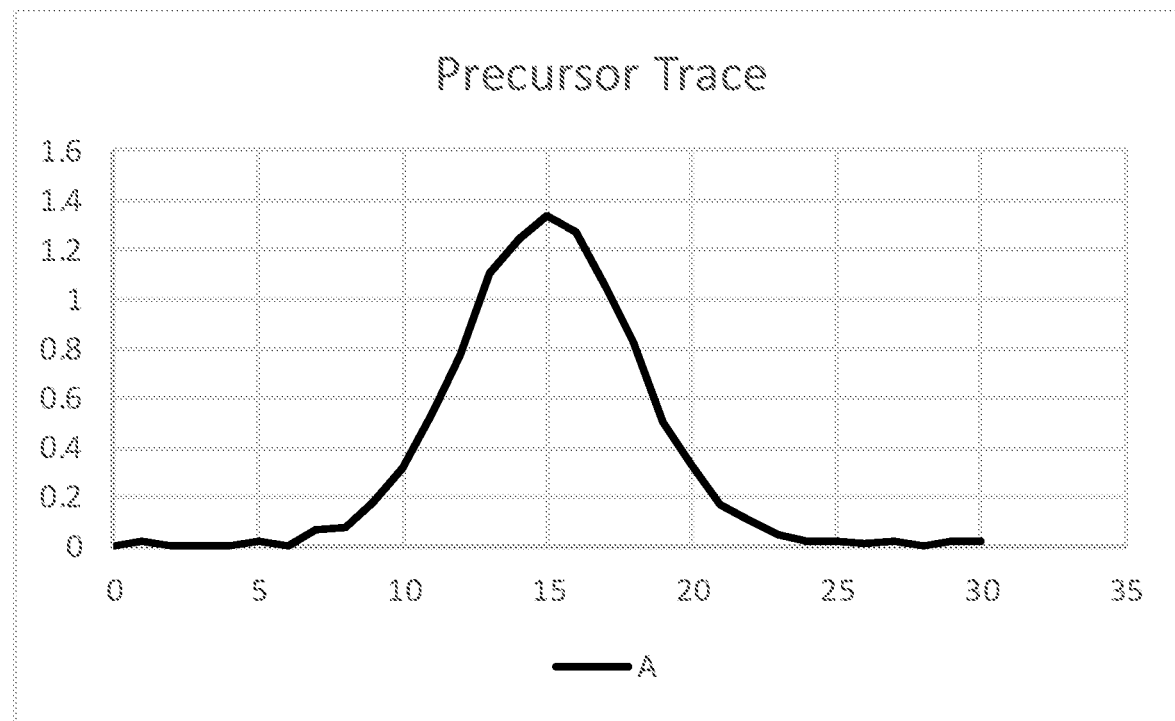
FIG. 5A is a graph illustrating a simulated precursor XIC.
Figure 5B:
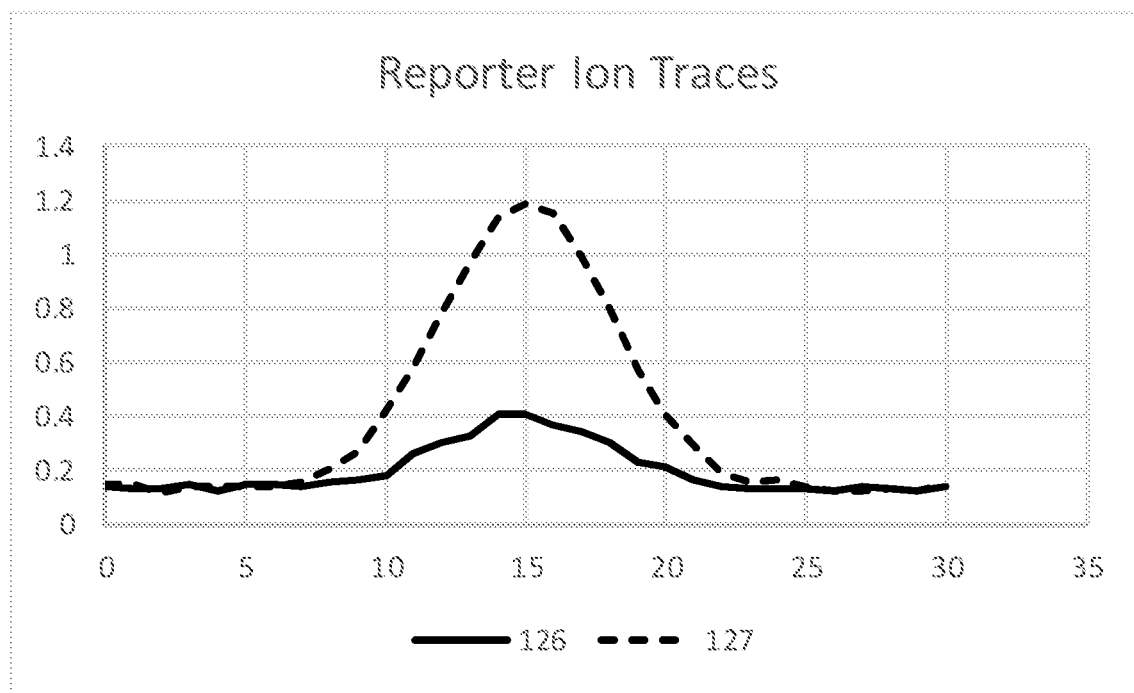
FIG. 5B is a graph illustrating XICs for simulated reporter ions.

The distorted ratios are demonstrated using an Excel simulation of a DIA experiment run with TMTDUPLEX reagents. The use of the disclosed method for reduction of ratio compression due to background ions (see Ting, Lily, et al. "MS3 eliminates ratio distortion in isobaric multiplexed quantitative proteomics." Nature methods 8.11 (2011): 937-940) is demonstrated. FIG. 5A shows simulated precursor ion extracted ion chromatograms (XIC) for a single component, and FIG. 5B shows simulated reporter ion XICs. The Gaussian peaks constructed using the NORMDIST( ) function, with random noise added to each trace. For the reporter ions, a constant reporter ion background of 1:1 is also added. The ratio between the concentration of the component in sample A (127 reporter ion) and the concentration of the component in sample 2 (126 reporter ion) is 4:1.

TABLE 1

127:126 Ratios for Single Component

|  | 127:126 Ratio |
|---|---|
| Area Ratio | 2.42 |
| Apex Ratio | 2.94 |
| Reconstructed Ratio | 3.99 |

Table 1 shows a comparison of the calculated ratios. In this case the ratio at the apex of the chromatographic peak is underestimated at 2.94, not the expected 4 and the ratio further compresses as one proceeds down the chromatographic peak resulting in an area ratio of 2.42. In contrast, using the disclosed reconstruction method, the ratio compression is suppressed resulting in a reconstructed ratio 3.99, compared to the expected 4 ratio. XICs for the reporter ions are effectively independent from one another, and thus can be processed individually to simplify the problem. The fitting process used is a simple least squares algorithm that finds the weights one reporter ion at a time.

Figure 6A:
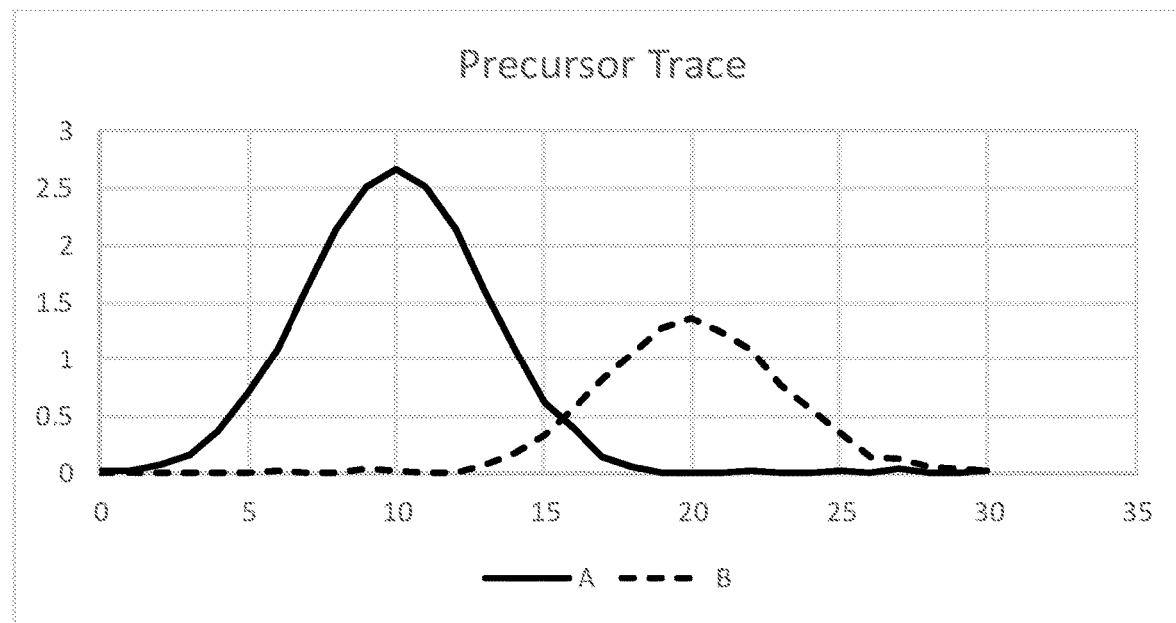
FIG. 6A is a graph illustrating XICs for simulated components A and B.
Figure 6B:
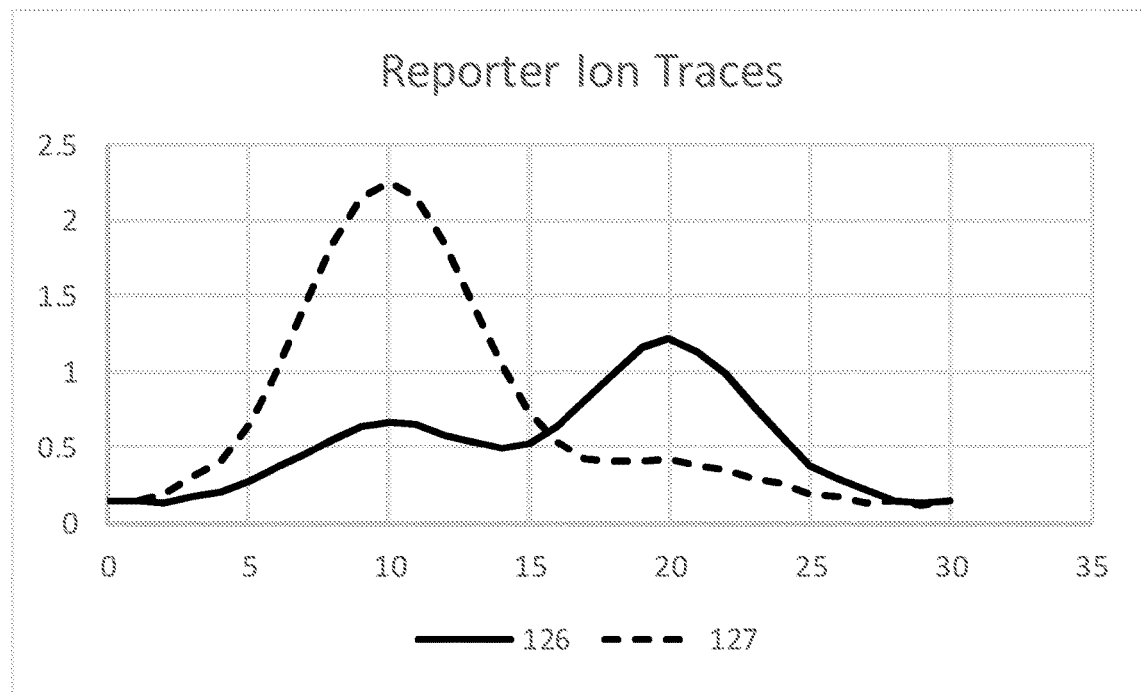
FIG. 6B is a graph illustrating XICs for simulated reporter ions.

FIG. 6A shows two overlapping Gaussian precursor peaks constructed, and FIG. 6B shows simulated (XICs) for the reporter ion regions. Component A has reporter ratios of 4:1 and component B has reporter ratios of 1:4. The Gaussian peaks constructed using the NORMDIST( ) function, with random noise added to each trace. For the reporter ions, a constant reporter ion background of 1:1 is also added. In the simulation, component A generates twice the abundance of reporter ions that component B generates. There is also random noise added to these traces.

TABLE 2

127:126 Ratios for Overlapping Components

|  | Component A 127:126 Ratio | Component B 127:126 Ratio |
|---|---|---|
| Expected Ratio | 4 | 0.25 |
| Area Ratio | 2.87 | 0.48 |

TABLE 2-continued

127:126 Ratios for Overlapping Components

|  | Component A 127:126 Ratio | Component B 127:126 Ratio |
|---|---|---|
| Apex Ratio | 3.38 | 0.34 |
| Reconstructed Ratio | 3.95 | 0.26 |

Table 2 shows the reporter ion ratios determined using various methods for components A and B. Again, the area ratio shows the greatest error, with a ratio of 2.87 for Component A (compared to the expected 4) and 0.48 for Component B (compared to the expected 0.25). While the Apex Ratio method shows improvement with 3.38 for Component A and 0.34 for Component B, there is still significant error. This is because of the interferences from the chromatographic overlap in combination with the reversed base reporter ion ratios. Using the disclosed reconstruction method, interferences from the chromatographic overlap is essentially eliminated with a ratio of 3.95 for Component A and 0.26 for Component B. The fitting process used is a simple least squares algorithm that finds the individual weights for components A and B, one reporter ion at a time.

What is claimed is:

1. An analysis system comprising:
   a separation instrument configured to perform a separation of compounds within a combined sample, the combined sample including a plurality of samples each labeled with a different isobaric tag;
   a mass spectrometer including:
      a mass selective device configured to isolate ions within a m/z range;
      a fragmentation cell configured to fragment the ions within the m/z range; and
      a ion detector configured to measure the intensities of structurally informative ions of a parent species and a plurality of reporter ions, the structurally informative ions resulting from fragmentation of a peptide backbone of the parent species; and
   a processor configured to:
      fit the intensities of the structurally informative ions and the plurality of reporter ions at a plurality of points along a peak to determine a contribution of interfering ions and a contribution quotient for the parent ions; and
      obtain a relative abundance of the parent species based on the contribution quotients for the parent ions for each of the plurality of samples.

2. The analysis system of claim 1 wherein the separation instrument includes a chromatographic separation device.

3. The analysis system of claim 1 wherein the separation instrument includes an electrophoretic separation device.

4. The analysis system of claim 1 wherein fitting includes performing a least squares fit.

5. The analysis system of claim 1 wherein the ion detector is further configured to determine intensities of structurally informative ions of a second parent species at the plurality of points, the plurality of points further including points along a second peak; and wherein the system controller is configured to fit to obtain a relative abundance by fitting the intensity of the structurally informative ions of the parent species, structurally informative ions of the second parent species, and the plurality of reporter ions at the first and second plurality of points.

6. The analysis system of claim 5 wherein the first and second peaks at least partially overlap.

7. A non-transitory computer readable medium containing instructions that when implemented by a processor perform the steps of:
  obtaining intensities data generated by a mass spectrometer for structurally informative ions of a parent species and a plurality of reporter ions at a plurality of points along a peak, the intensity data collected from a combined sample that has undergone a separation of compounds within the sample, the combined sample including a plurality of samples each labeled with a different isobaric tag, the structurally informative ions resulting from fragmentation of a peptide backbone of the parent species; and
  fitting the intensity data of the structurally informative ions and the plurality of reporter ions at a plurality of points along a peak to determine a contribution of interfering ions and a contribution quotient for the parent ion; and
  obtain a relative abundance of the parent species based on the contribution quotients for the parent ions for each of the plurality of samples.

8. The non-transitory computer readable medium of claim 7 wherein the separation is a chromatographic separation and the peak is a chromatographic peak.

9. The non-transitory computer readable medium of claim 7 wherein the separation is an electrophoretic separation and the peak is an electrophoretic peak.

10. The non-transitory computer readable medium of claim 7 wherein fitting includes performing a least squares fit.

11. The non-transitory computer readable medium of claim 7 further comprising:
  using the mass spectrometer to obtain intensity data for structurally informative ions of a second parent species at the plurality of points, the plurality of points further including points along a second peak; and
  fitting the intensity data of the ions representative of the parent species, the ions representative of the second parent species, and the plurality of reporter ions at the plurality of points to obtain a relative abundance of the parent species and the second parent species in each of the plurality of samples.

12. The non-transitory computer readable medium of claim 11 wherein the first and second peaks at least partially overlap.

* * * * *